United States Patent [19]

Schulte et al.

[11] Patent Number: 4,552,553
[45] Date of Patent: Nov. 12, 1985

[54] FLOW CONTROL VALVE

[75] Inventors: Rudolf R. Schulte; Gary P. East, both of Santa Barbara; Marga M. Bryant; Alfons Heindl, both of Goleta, all of Calif.

[73] Assignee: Pudenz-Schulte Medical Research Corp., Santa Barbara, Calif.

[21] Appl. No.: 574,997

[22] Filed: Jan. 30, 1984

Related U.S. Application Data

[63] Continuation of Ser. No. 510,381, Jun. 30, 1983, abandoned, which is a continuation of Ser. No. 208,514, Nov. 20, 1980, abandoned.

[51] Int. Cl.[4] ............................................. A61M 5/00
[52] U.S. Cl. ....................................................... 604/9
[58] Field of Search .................... 604/8, 9, 10, 175; 3/1

[56] References Cited

U.S. PATENT DOCUMENTS

| 2,867,213 | 1/1959 | Thomas . | |
|---|---|---|---|
| 2,933,102 | 4/1960 | Hillman et al. . | |
| 3,021,842 | 2/1962 | Flood | 604/175 |
| 3,111,125 | 11/1963 | Schulte . | |
| 3,288,142 | 11/1966 | Hakim . | |
| 3,444,861 | 5/1969 | Schulte | 604/175 X |
| 3,492,996 | 2/1970 | Fountain . | |
| 3,503,402 | 3/1970 | Schulte . | |
| 3,527,226 | 9/1970 | Hakim . | |
| 3,595,240 | 7/1971 | Mishler . | |
| 3,601,128 | 8/1971 | Hakim . | |
| 3,756,243 | 9/1973 | Schulte . | |
| 3,758,073 | 9/1973 | Schulte . | |
| 3,768,508 | 10/1973 | Schulte . | |
| 3,769,982 | 11/1973 | Schulte . | |
| 3,827,439 | 8/1974 | Schulte et al. . | |
| 3,851,588 | 12/1974 | Taylor . | |
| 3,901,245 | 8/1975 | Spitz et al. | 604/10 |
| 3,980,097 | 9/1976 | Ellis . | |
| 3,999,553 | 12/1976 | Spitz et al. | 604/10 |
| 4,084,606 | 4/1978 | Mittleman . | |
| 4,364,395 | 12/1982 | Redmond et al. . | |

OTHER PUBLICATIONS

Brochure: The Surgical Treatment of Hydrocephalus-An Historical Review, Date: 1/1/81, Author: Robert H. Pudenz, M.D.
Brochure: Silastic Hydrocephalus Shunt, Date: 12/72, Author: Dow Corning.
Brochure: Holter-Hausner International.
Brochure: Accu-Flow Valve System-Hydrocephalus Shunt Systems, Copyright: 1981, Author: Codman.

Primary Examiner—Clifford D. Crowder
Attorney, Agent, or Firm—Fulwider, Patton, Rieber, Lee & Utecht

[57] ABSTRACT

For use in controlling the release of entrapped body fluids, a surgically implantable flow control valve is provided which includes a molded plastic base separating an inlet chamber from an outlet chamber and including one or more apertures passing from the inlet chamber to the outlet chamber, and a resilient membrane which is molded of a material different from the material of the plastic base and which is secured to the base covering the aperture or apertures through the base on the outlet chamber side of the base.

29 Claims, 2 Drawing Figures

FLOW CONTROL VALVE

This is a continuation of application Ser. No. 510,381, filed June 30, 1983 which is a continuation of Ser. No. 208,514, filed Nov. 20, 1980 (Both Now Abandoned).

BACKGROUND OF THE INVENTION

This invention relates generally to surgically implantable valves, and more particularly, to improvements in one-way flow control valves for controlling the flow of cerebrospinal fluid out of a brain ventricle and preventing backflow of fluid into the brain ventricle.

As is well known in the medical arts, to relieve undesirable accumulation of fluids, it is frequently necessary to provide a means for draining a fluid from one part of the human body to another in a controlled manner. This is required, for example, in the treatment of hydrocephalus, an ailment, usually afflicting infants or children, in which fluids which ought to drain away accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart atrium.

Many such devices have been used heretofore, but prior devices have tended to become obstructed by particulate matter entering the drainage system or by the backward diffusion of blood into the system. Further, some prior devices have included moving parts which tend to share to adhere to other parts of the device and become immobile. When this occurs, the device itself becomes a barrier in the drainage system, and it adds to the problem it is intended to solve. Moreover, some prior devices have included metal components which tended to interfere with X-ray photography, and X-ray photography frequently accompanies the use of surgically implanted flow control valves.

Accordingly, there has been a long existing need in the medical arts for a convenient and effective device for controlling the flow of fluid from one part of the human body to another, which device is relatively inexpensive to manufacture and which is constructed of non-metallic parts which are not subject to adhering to one another and causing malfunction of the device. All will become apparent from the following description, the present invention satisfies these needs and provides other related advantages.

SUMMARY OF THE INVENTION

The present invention resides in a device for controlling the flow of fluids from one part of the human body to another, which device is constructed of non-metallic materials which prevent adhesion of one part to another, thereby providing trouble-free and reliable operation of the device. Moreover, the apparatus of the present invention is relatively inexpensive to manufacture, and can be easily modified to provide a variety of pressure/flow characteristics.

The illustrated device of the present invention is constructed of a relatively rigid, unitized molded plastic base having apertures through which the fluid must flow and a resilient membrane, molded of a non-metallic material different from the material of the plastic base, which membrane covers the apertures through the base on the downstream side of the base. The resilient membrane is normally biased to prevent flow through the valve, but will open to permit flow through the valve when the pressure upstream of the valve exceeds the pressure downstream of the valve by a predetermined amount.

More specifically, the plastic base separates an inlet chamber covered by a resilient dome from an outlet chamber, and the apertures through the base permit flow from the inlet chamber to the outlet chamber. To permit connection of the valve of the present invention to a conduit of a drainage system, an inlet connector and an outlet connector are integrally molded with a generally horizontal plate to form the unitized base, and the inlet and outlet connectors are in open communication with the inlet chamber and the outlet chamber, respectively. The resilient membrane is secured to the base and overlies the apertures through the base on the outlet chamber side of the base.

A variety of pressure/flow characteristics can be provided by the flow control valve of the present invention by providing the valve with a resilient membrane having a different thickness. The resistance to flow through the valve increases with increase in membrane thickness.

In order to provide the desired resistance to adhesion between the plastic base and the resilient membrane, particularly during storage of the valve, the plastic base is preferably formed of a polypropylene material, and the membrane is preferably formed of a silicone elastomer material. Further, the resilient dome which cooperates with the plastic base to form the inlet chamber is also preferably molded of a silicon elastomer material.

Other features and advantages of the present invention will become apparent from the following more detailed description, taken in conjunction with the accompanying drawings, which illustrate, by way of example, the principles of the invention.

DETAILED DESCRIPTION

Figure 1:
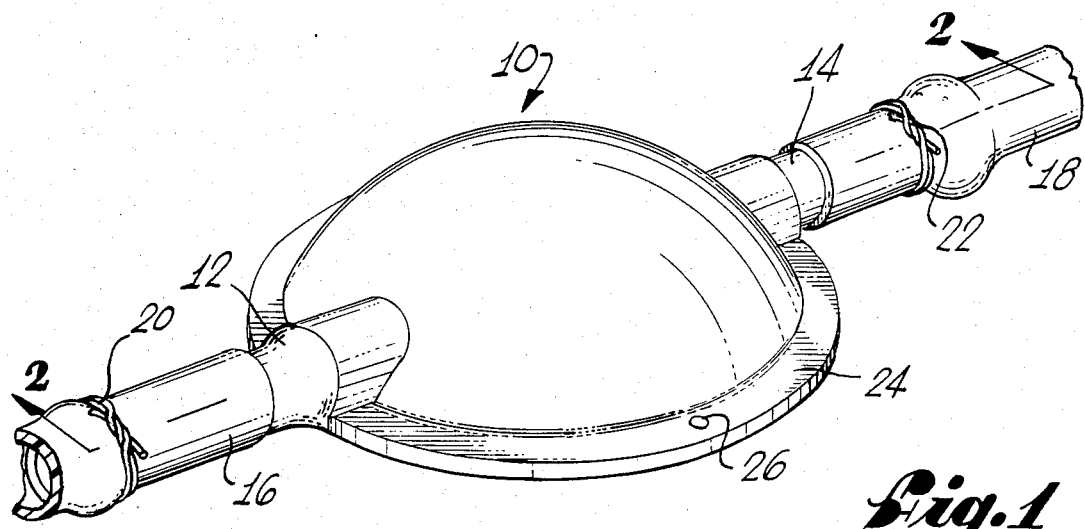
FIG. 1 is a perspective view of a preferred form the flow control valve of the present invention shown connected to surgical tubing, the tubes being shown in fragmentary form.

As shown in the drawings for purposes of illustration, the present invention is embodied in a flow control valve, indicated generally by reference numeral 10 in FIG. 1, intended for use in a surgically implanted system for draining fluid from one portion of the human body to another. In order to connect the valve 10 in such a system, the valve includes an inlet connector 12 and an outlet connector 14 which each receive one end of a piece of surgical tubing, illustrated in FIG. 1 as an inlet tube 16 and an outlet tube 18. The tubes 16 and 18 slide over the connectors 12 and 14, and each is secured to its respective connector by a single ligature 20 and 22. The ligatures are preferably secured around the tubing just inside of an annular ridge 23 formed near the end of each connector (FIG. 2).

When the valve 10 is used in a drainage system intended for treatment of hydrocephalus, the inlet tube 16 connects to a proximal catheter (not shown) which is inserted through the skull into a brain ventricle containing cerebrospinal fluid under pressure. The outlet tube 18 connects to a distal catheter (not shown) which serves to discharge cerebrospinal fluid into, for example, the atrium portion of a patient's heart. Ordinarily, a valve 10 will be surgically implanted on the patient's skull with a flap of skin overlying the valve. To facilitate holding the valve in its desired position after implantation, a generally flexible mounting plate 24 of the valve can be provided with one or more suture holes 26.

Figure 2:
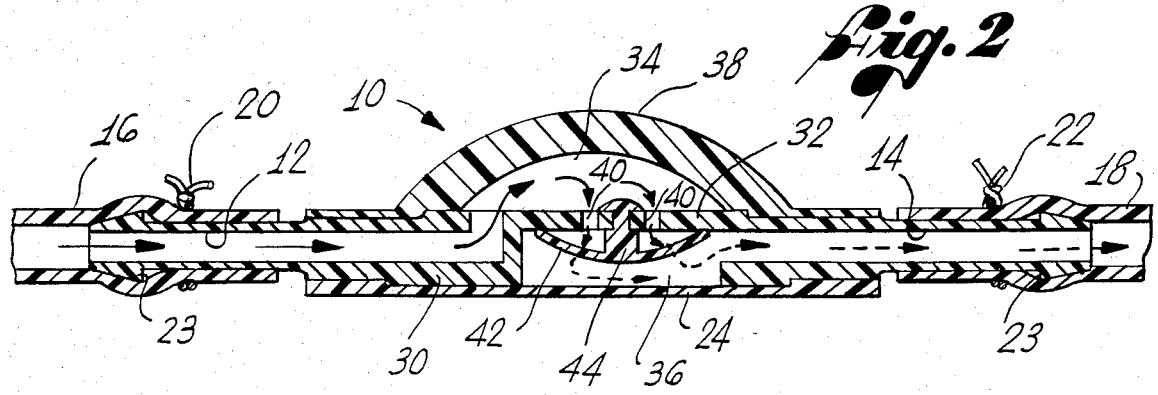
FIG. 2 is an elevational, sectional view of the flow control valve of the present invention, taken substantially along line 2—2 of FIG. 1, and including arrows indicating the direction of fluid flow through the valve.

In accordance with the present invention, and as best shown in FIG. 2, the valve 10 includes a relatively rigid, molded plastic base 30 of unitized construction. The base 30 comprises a generally horizontal plate 32, which separates an inlet chamber 34 from an outlet chamber 36 in the valve 10, and the inlet and outlet connectors 12 and 14 which are integrally formed with the plate.

The inlet chamber 34 is defined generally by the top of the plate 32 and a resilient dome 38 secured to the top of the base 30. The outlet chamber 36 is defined generally by the bottom of the plate 32 and the mounting plate 24. It will be noted that the inlet connector 12 is in open communication with the inlet chamber 34, and the outlet connector 14 is in open communication with the outlet chamber 36. To permit fluid to flow through the valve 10, one or more apertures 40 are provided through the plate 32.

The flow control valve 10 is arranged for controlling the flow of cerebrospinal fluid out of a brain ventricle and preventing backflow of fluid into the brain ventricle by the provision of a resilient non-metallic membrane 42, which is molded of a synthetic polymer material different from the material of the relatively rigid plastic base, and which is secured to the base and covers the aperture or apertures 40 on the outlet chamber side of the base. The resilient membrane 42 is normally biased to close communication from the inlet chamber to the outlet chamber, but will open to permit flow (as indicated by the arrows in FIG. 2) when the pressure in the inlet chamber exceeds the pressure in the outlet chamber by a predetermined amount. Moreover, should the pressure in the outlet chamber ever exceed the pressure in the inlet chamber, tending to cause flow in a reverse direction through the valve, the membrane 42 will seal tightly against the plate 32, sealing the apertures 40 and preventing any such reverse flow.

More specifically, the molded plastic base of the present invention is preferably formed of a polypropylene material, and the membrane 42 is formed of an elastomer material, preferably a silicone elastomer material. Both the polypropylene and elastomer materials have been shown to produce an acceptable level of tissue reaction, and it has been discovered that the use of this particular duality of materials, in contrast to use of only a single material by the prior art, markedly decreases the chance of the membrane 42 adhering to the base 30, which would clog the drain passage and defeat the whole purpose of the valve 10. Further, the valve of this invention is relatively inexpensive to manufacture, is trouble-free and reliable in use, and can be easily modified to produce a variety of pressure/flow characteristics.

An added advantage of using these particular materials is the avoidance of the negative effect of metal components, due to radiation scatter or "sunburst effect", on films taken by, for example, computerized axial tomography (CAT) scanning equipment. This type of scanning frequently accompanies the use of surgically implanted flow control valves, and the absence of metal in the area scanned will permit more accurate and complete results to be gathered from CAT scanning.

In the preferred embodiment illustrated, the membrane 42 has an arch-shape, as for example a section of a sphere, and contacts the lower side of the plate 32 generally along the outer edges of the membrane in a manner surrounding the apertures 40. The membrane 42 is secured to the plate 32 by an upstanding central support 44 which is received in a mounting aperture in the plate and fixed thereto by an interference fit and use of an adhesive, or any other suitable means.

Since the valve 10 of the present invention is primarily designed to provide controlled resistance to cerebrospinal fluid flow from a brain ventricle to an atrium portion of the patient's heart, it will be appreciated that a doctor must be able to select a valve having the particular pressure/flow characteristics desired for each individual application. That is, a valve which permits flow at a relatively low pressure differential may not be suitable where the maintenance of a higher pressure differential is indicated.

Toward this end, in order to provide a variety of valves having different pressure/flow characteristics the valve 10 can be provided with a thick membrane 42 or a relatively thin membrane 42. Resistance to flow increases with the increase in membrane thickness.

The resilient dome 38 is also preferably molded of a silicone elastomer material, and is designed to permit injection into the drainage system by a hypodermic needle through the dome. Further, the dome 38 is sufficiently resilient to be deformed downwardly by external finger pressure. In this way, the flow control valve 10 can be flushed manually in either the proximal or distal direction.

To flush the control valve 10 in the proximal direction, the outlet tube 18 can be occluded by finger pressure, and the dome 38 pressed downwardly as described above. The occlusion of the outlet tube 18 prevents any flow from the valve in the distal direction, and the depression of the dome 38 will therefore cause flushing of the fluid in the valve in the proximal direction. Similarly, by occluding the inlet tube 16 and depressing the dome 38, fluid in the inlet chamber 34 will be forced through the apertures 40, past the membrane 42 and into the outlet tube 18.

From the foregoing, it will be appreciated that the valve 10 of the present invention provides a device by which the flow of cerebrospinal fluid out of a brain ventricle can be controlled while preventing the backflow of fluid into the brain ventricle, and by which the chance of the valve clogging the drain passage can be greatly decreased. Further, the valve 10 can be fabricated conveniently and economically, is trouble-free and reliable in use, and can be easily adapted to provide a variety of pressure/flow characteristics.

While a particular form of the invention has been illustrated and described, it will be apparent that various modifications can be made without departing from the spirit and scope of the invention. Accordingly, it is not intended that the invention be limited, except as by the appended claims.

We claim:

1. A surgically implantable flow control valve for controlling the flow of fluid from one portion of the human body to another, said valve comprising:

a substantially rigid polypropylene base of unitized construction including a plate having a generally planar inlet surface and a generally planar outlet surface, a tubular inlet connector integral with said plate, and a tubular outlet connector integral with said plate;

an inlet passageway through said base, said inlet passageway originating at an open end of said inlet connector and terminating at an inlet port situated on said inlet surface of said plate;

an outlet passageway through said base, said outlet passageway originating at an outlet port adjacent said outlet surface and terminating at an open end of said outlet connector;

a resilient dome substantially overlying said base and said inlet port, said dome having an arch-shape similar to one-half of a sphere, the inner surface of said dome being smooth and forming a seal against an upper surface of said base to create an inlet chamber between said dome and said base, said dome being deformable toward said base by external pressure so that the extent of deformation is limited by contact between said dome and said base;

a mounting pad generally underlying said base and interacting with the edges of said dome to substantially encase said base in connection with said dome, said mounting pad including suture holes to allow said valve to be fixedly attached to a specific location on the human body;

an outlet chamber between said outlet surface and said mounting pad;

a plate passageway permitting fluid communication between said inlet chamber and said outlet chamber; and a flow control member including a central support and a resilient membrane, said central support being securely attached to said base and extending therefrom into said outlet chamber to support said membrane, said membrane being generally arch-shaped and resiliently biased to normally contact said outlet surface generally along the outer edges of said membrane in a manner surrounding said plate passageway and forming a releasable seal between said outlet surface and the outer edges of said membrane, said outlet surface being sufficiently rigid to maintain a proper valve seat for the outer edges of said membrane despite pressure applied to said inlet surface caused by contact of said dome with said inlet surface when said dome is fully deformed, said membrane being formed of an elastomer material to prevent sticking with said polypropylene base.

2. A surgically implantable flow control valve, comprising:
an inlet;
an outlet;
a rigid base forming a wall separating said inlet from said outlet, said wall including a planar valve seat on its outlet side;
an aperture through said wall for permitting fluid flow through said valve from said inlet to said outlet; and
a flow control member including a central support and a resilient membrane, said central support being securely attached to said wall adjacent said aperture and extending therefrom on the outlet side of said wall to support said membrane, said membrane being generally arch-shaped and resiliently biased to normally contact said planar valve seat generally along the outer edges of said membrane in a manner surrounding said aperture and forming a releasable seal between the outlet side of said wall and the outer edges of said membrane.

3. A valve as recited in claim 2 wherein said membrane is molded of a non-metallic synthetic polymer material different from the material of said base.

4. A valve as recited in claim 3 wherein said base is formed of a polypropylene material.

5. A valve as recited in claim 4 wherein said membrane is formed of an elastomer material.

6. A valve as recited in claim 2 including a flexible encasement generally surrounding said base.

7. A valve as recited in claim 6 wherein said encasement is deformable toward the inlet side of said wall by external pressure primarily to facilitate manual flushing of said valve.

8. A valve as recited in claim 7 wherein said central support holds said membrane adjacent the outlet side of said wall in a manner permitting full deformation of said encasement toward the inlet side of said wall without affecting the seal between the outer edges of said membrane and said wall.

9. A valve as recited in claim 7 wherein said base is sufficiently rigid to maintain said valve seat for said membrane despite external pressure applied to the inlet side of said wall when said encasement is fully deformed.

10. A valve as recited in claim 2 further including a resilient dome secured to said base over the inlet side of said wall to form an inlet chamber in communication with said inlet, said dome being deformable toward said wall by external pressure.

11. A surgically implantable flow control valve for controlling the flow of fluid from one portion of the human body to another, said valve comprising:

an inlet substantially defined by an inlet connector and an inlet chamber;

an outlet substantially defined by an outlet connector and an outlet chamber;

a base of unitized construction including a rigid plate which resists deformation and which is integrally formed with said inlet and outlet connectors, said plate having a planar inlet surface in communication with said inlet chamber and a parallel planar outlet surface in communication with said outlet chamber, said outlet surface providing a planar valve seat within said valve;

an aperture through said plate for permitting flow of the fluid through said valve from said inlet chamber to said outlet chamber, said aperture being situated in the vicinity of said valve seat; and a flow control member mounted adjacent said outlet surface and over said aperture, said member being resiliently biased to overlie and close said aperture to fluid flow, the rigidness of said base facilitating the formation of a releasable seal between said member and said valve seat.

12. A valve as recited in claim 11 wherein said member is molded of a non-metallic synthetic polymer material different from the material of said base.

13. A valve as recited in claim 12 wherein said base is formed of a polypropylene material.

14. A valve as recited in claim 13 wherein said member is formed of an elastomer material.

15. A valve as recited in claim 11 including a flexible encasement generally surrounding said base and including means for anchoring said valve.

16. A valve as recited in claim 15 wherein said encasement is deformable toward said inlet surface by external pressure primarily for causing manual flushing of said valve.

17. A valve as recited in claim 16 wherein said member is held adjacent said outlet surface in a manner permitting full deformation of said encasement toward said inlet surface without affecting the seal between said member and said valve seat.

18. A valve as recited in claim 17 wherein said flow control member includes a central support and a resilient membrane, said central support being securely attached to said outlet surface and extending therefrom into said outlet chamber to support said resilient membrane, said resilient membrane being generally arch-shaped so that the outer edges of said membrane normally contact said outlet surface in a manner surrounding said aperture.

19. A valve as recited in claim 11 further including a resilient dome secured to said inlet surface and cooperating with said inlet surface to form said inlet chamber, said dome being deformable toward said inlet surface by external pressure.

20. A surgically implantable flow control valve for controlling the flow of fluid from one portion of the human body to another, said valve comprising:
- a base of unitized construction including a substantially rigid base plate having a first surface and a second surface, an inlet connector integral with said plate, and an outlet connector integral with said plate;
- an inlet passageway through said base, said inlet passageway originating at an open end of said inlet connector and terminating at an inlet port;
- an outlet passageway through said base, said outlet passageway originating at an outlet port adjacent said second surface and terminating at an open end of said outlet connector;
- an inlet chamber adjacent said first surface, said inlet chamber communicating with said inlet passageway at said inlet port;
- an outlet chamber adjacent said second surface, said second surface including a planar valve seat and said outlet chamber communicating with said outlet passageway at said outlet port;
- a base plate passageway permitting communication between said inlet chamber and said outlet chamber; and
- a flow control member including a central support and a resilient membrane, said central support being securely attached to said base plate and extending therefrom into said outlet chamber to support said membrane, and said membrane being generally arched-shaped and resiliently biased to normally contact said second surface generally along the outer edges of said membrane in a manner surrounding said base plate passageway.

21. A valve as recited in claim 20 wherein said membrane is molded of a non-metallic synthetic polymer material different from the material of said base.

22. A valve as recited in claim 20 wherein said base is formed of a polypropylene material.

23. A valve as recited in claim 22 wherein said membrane is formed of a silicone elastomer material.

24. A valve as recited in claim 20 including a dome deformable toward said base by external finger pressure.

25. A valve as recited in claim 24 wherein said central support holds said membrane adjacent said second surface and within said outlet chamber in a manner permitting full deformation of said dome toward said first surface without affecting a seal formed between the outer edge of said membrane and said second surface.

26. A valve as recited in claim 24 wherein said base is sufficiently rigid to maintain said valve seat for said membrane on said second surface despite external pressure applied to said first surface when said dome is fully deformed.

27. A valve as recited in claim 20 wherein said outlet chamber is defined by a hollow void in said base situated between said second surface and said outlet port.

28. A valve as recited in claim 27 wherein said outlet chamber includes a generally open side which is enclosed by a mounting pad affixed to the underside of said base.

29. A valve as recited in claim 27 wherein said outlet chamber is substantially surrounded by said base so that fluid can only enter said outlet chamber through said base plate passageway and exit said outlet chamber through said outlet port.

* * * * *